US009486752B2

(12) United States Patent
Haroun et al.

(10) Patent No.: US 9,486,752 B2
(45) Date of Patent: Nov. 8, 2016

(54) DISTRIBUTOR PLATE FOR A GAS-LIQUID MIXTURE, PROVIDED WITH DISTRIBUTION ELEMENTS HAVING LOW SENSITIVITY TO A LACK OF HORIZONTALITY

(71) Applicant: IFP Energies nouvelles, Rueil-Malmaison (FR)

(72) Inventors: Yacine Haroun, Grigny (FR); Frederic Bazer-Bachi, Irigny (FR); Frederic Augier, Saint Symphorien d Ozon (FR); Charly Rogeon, Bourgoin Jallieu (FR); Christophe Boyer, Charly (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 260 days.

(21) Appl. No.: 14/356,252

(22) PCT Filed: Oct. 9, 2012

(86) PCT No.: PCT/FR2012/000407
§ 371 (c)(1),
(2) Date: Jul. 17, 2014

(87) PCT Pub. No.: WO2013/064756
PCT Pub. Date: May 10, 2013

(65) Prior Publication Data
US 2014/0364650 A1 Dec. 11, 2014

(30) Foreign Application Priority Data
Nov. 3, 2011 (FR) ...................................... 11 03336

(51) Int. Cl.
*B01F 3/00* (2006.01)
*B01F 3/04* (2006.01)
(Continued)

(52) U.S. Cl.
CPC ........... *B01F 3/04468* (2013.01); *B01D 3/008* (2013.01); *B01D 3/20* (2013.01);
(Continued)

(58) Field of Classification Search
CPC ..................................... B01F 3/04; B01F 3/00
USPC .................... 261/110, 114.1, 114.2; 422/176
See application file for complete search history.

(56) References Cited

U.S. PATENT DOCUMENTS

| | | | |
|---|---|---|---|
| 6,769,672 B2 * | 8/2004 | Muller | B01D 3/20 261/110 |
| 7,600,742 B2 | 10/2009 | Breivik | |

(Continued)

FOREIGN PATENT DOCUMENTS

| | | |
|---|---|---|
| WO | 2005068039 A1 | 7/2005 |
| WO | 2007023225 A1 | 3/2007 |

OTHER PUBLICATIONS

International Search Report for PCT/FR2012/000407 dated Jan. 24, 2013.

*Primary Examiner* — Robert A Hopkins
(74) *Attorney, Agent, or Firm* — Millen White Zelano and Branigan, PC; Csaba Henter; Anthony Zelano (57) ABSTRACT

The present invention describes a distributor plate provided with distribution elements having low sensitivity to a lack of horizontality, a distribution element being constituted by two substantially co-axial cylinders termed the inner cylinder (1) and the outer cylinder, the lower horizontal surface (5) separating the two cylinders being closed. The distributor plate is suitable for co-current downflows of gas and liquid, more particularly in "trickle bed" mode. The invention also concerns the application of the distributor plate to processes for the hydrotreatment or hydrogenation of various oil cuts.

19 Claims, 6 Drawing Sheets

(51) Int. Cl.
*B01D 3/20* (2006.01)
*B01J 8/04* (2006.01)
*B01J 8/02* (2006.01)
*B01D 3/00* (2006.01)
*C07B 33/00* (2006.01)
*C10G 45/00* (2006.01)
*C10G 49/00* (2006.01)

(52) U.S. Cl.
CPC .................. *B01F 3/00* (2013.01); *B01F 3/04* (2013.01); *B01J 8/025* (2013.01); *B01J 8/0278* (2013.01); *B01J 8/0453* (2013.01); *B01J 8/0492* (2013.01); *C07B 33/00* (2013.01); *C10G 45/00* (2013.01); *C10G 49/00* (2013.01)

(56) References Cited

U.S. PATENT DOCUMENTS

| | | |
|---|---|---|
| 8,329,974 B2 | 12/2012 | Koudil et al. |
| 2006/0163758 A1 | 7/2006 | Muller et al. |
| 2007/0145610 A1 | 6/2007 | Breivik |
| 2009/0177023 A1 | 7/2009 | Koudil et al. |
| 2013/0064727 A1 | 3/2013 | Koudil et al. |

* cited by examiner

DISTRIBUTOR PLATE FOR A GAS-LIQUID MIXTURE, PROVIDED WITH DISTRIBUTION ELEMENTS HAVING LOW SENSITIVITY TO A LACK OF HORIZONTALITY

The present invention relates to the field of gas and liquid distribution in fixed bed type catalytic reactors operating in co-current gas/liquid downflow mode. The principal envisaged application is the hydrotreatment of gas oil or other oil cuts, and more generally any processes using one or more reactors operating in gas/liquid downflow mode.

The vast majority of existing distributors are composed of a plate provided with distribution elements such as those described, for example, in the article "Gas-liquid distributors for trickle bed reactors: A Review", by R N Maiti and K D P Nigam, Ind Eng Chem Res 2007, 46, 6464-6182.

Such chimneys may be of various types and positioned in various configurations on the plate, as described in patents US2002/0127160A1, U.S. Pat. No. 6,093,373, US2004/0197245A1, US2007/0241467A1, GB721247, U.S. Pat. No. 658,738, US2007/145610 and U.S. Pat. No. 5,942,162.

The aim of a distributor plate placed upstream of a catalytic bed in a reactor operating in co-current gas and liquid downflow mode is to distribute the two-phase mixture of gas and liquid as homogeneously as possible over the catalytic bed located downstream thereof. At the outlet from the chimneys of the plate, the flow of two-phase mixture generally forms a concentrated jet.

Prior art distributor plates equipped with perforated chimneys operate on the basis of gravitational flow. The liquid is distributed by passing liquid into orifices generally distributed along the lateral walls of the chimneys and gas is distributed via the opening at the top of the chimney. However, a lack of horizontality may occur in such a plate due to flexing of the plate under its own weight or a shift of said plate with respect to the horizontal plane when it is being installed.

In the presence of a lack of horizontality of the plate, the height of the liquid trap is no longer uniform over the distributor plate, which results in imbalances in the distribution of liquid over the downstream catalytic bed, in particular when the level of the liquid is close to a row of orifices.

Prior art distributor plates provided with "bell-cap" chimneys are also sensitive to a lack of horizontality of the plate. A bell-cap chimney is constituted by a central cylinder surmounted by a bell-cap provided with a plurality of slots. The gas and liquid pass through via the slots and via the bottom of the bell-cap, and also in the space between the bell-cap and the principal cylinder. Other variations on the bell-cap chimney exist, such as "vapour-lift" chimneys (patents US2007/145610, U.S. Pat. No. 5,942,162), but the operating principle remains the same.

The operation of "bell-cap" chimneys is based on entraining liquid by gas across the space between the bell-cap and the cylinder. However, in the presence of a lack of horizontality of the plate, the height of the liquid trap is no longer uniform over the distributor plate. The distance between the surfaces open to gas between two offset chimneys thus becomes relatively large and liquid entrainment is no longer homogeneous between the chimneys, which causes substantial mal-distribution of liquid. The principal aggravating factors of this phenomenon are the opening at the bottom of the bell-cap and the large number of slots.

If it is not controlled, this mal-distribution may substantially degrade the performance of the reactor.

BRIEF DESCRIPTION OF THE INVENTION

The aim of the present invention is to improve the quality of distribution of prior art distributor plates by providing them with distribution elements with a lower sensitivity to a lack of horizontality than that of perforated chimneys and bell-cap chimneys of the prior art, as well as better flexibility in operation.

The distributor plate of the present invention is composed of a multiplicity of distribution elements distributed regularly over said plate in a rectangular, square or triangular pattern.

The distribution element of the distributor plate of the present invention is composed of two cylindrical tubes which are approximately concentric and vertical, the outer cylindrical tube being provided with one or more slots for the passage of gas and liquid.

The two concentric tubes are intended to determine an annular mixing zone for the gas and liquid and allow the resulting gas/liquid mixture to be reintroduced at different points of the section of the reactor in as homogeneous a manner as possible.

The outer cylindrical tube is raised with respect to the plane of the plate, which means that a height h3 can be defined, forming a protection for the liquid admission slot or slots against possible fouling due to impurities which may be contained in the liquid feed, particularly when it is a heavy hydrocarbon feed. Raising the outer cylinder also means that the bulk in the plane of the plate can be reduced, with the advantage that liquid is distributed better over the distributor plate.

Unlike the operation of prior art plates, the operation of the distribution elements of the invention is principally based on entraining liquid in the rising part of the annular space separating the two coaxial cylinders under the effect of the flow of the gas phase. The flow in the annular space passes exclusively via the surface located on the lateral wall, which ensures better control of the dry slot (section open to the flow of gas) and thus renders the plate of the invention less sensitive to a lack of horizontality.

One of the advantages of the present invention is that the height of the dry slot is always sufficient to allow homogeneous admission of gas into the annular zone and eventually to allow balanced entrainment of liquid between the chimneys.

In practice, the use of this novel distribution element means that on average, over a large liquid range, the sensitivity to a lack of horizontality of the plate can be reduced.

More precisely, the present invention may be defined as a distributor plate for a gas-liquid flow in downflow co-current mode positioned at various levels of a reactor which may comprise a plurality of catalytic beds, in order to ensure homogeneous distribution of the resulting gas-liquid mixture over a catalytic bed located downstream of said plate, said plate being provided with distribution elements distributed regularly over the surface of the plate in a square or triangular pattern.

A distribution element is constituted by two substantially coaxial cylinders termed the inner cylinder 1 with a diameter d1 and height h1, and the outer cylinder 2 with a diameter d2 and height h2, the lower horizontal surface 5 separating the two cylinders being closed.

The lateral wall of the outer cylinder 2 is provided with at least one substantially vertical slot 4 for admitting gas and liquid into the annular zone 3. The gas-liquid mixture is entrained in the annular zone 3 as an upflowing stream, then passes into the inner cylinder 1 via the upper opening 6 thereof and drops inside the inner cylinder 1, then is evacuated via the opening 7 located at the lower end of the inner cylinder 1.

In accordance with the invention, the closed horizontal surface 5 of the distribution element is located above the base of the distributor plate at a height h3 in the range 10 to 100 mm, preferably in the range 20 mm to 60 mm.

The number of vertical slots 4 with height h4 is preferably in the range 1 to 3, and more preferably in the range 1 to 2.

The pitch between the distribution elements is preferably in accordance with a square or triangular pattern in the range 100 to 300 mm, more preferably in the range 100 to 200 mm.

The total height of the distribution elements, counted from the base of the distributor plate, is in the range 100 to 500 mm, preferably in the range 200 to 400 mm.

The principal dimensions of the distribution elements are denoted as follows:
height of outer cylinder, h2:
diameter of outer cylinder, d2:
height of inner cylinder, h1:
diameter of inner cylinder, d1:
height of the admission slot for the gas-liquid mixture, h4:
width of the admission slot for the gas-liquid mixture, ef:
height of the outer cylinder with respect to the base plane of the plate, h3:

The values for these principal dimensions are in the following ranges:
h2 is in the range 100 to 500 mm, preferably in the range 200 to 400 mm;
d2 is in the range 15 to 300 mm, preferably in the range 50 to 200 mm;
h1 is in the range 100 to 500 mm, preferably in the range 200 to 400 mm;
d1 is in the range 10 to 100 mm, preferably in the range 25 to 75 mm;
h4 is in the range 10 to 500 mm, preferably in the range 100 to 300 mm;
ef is in the range 1 to 5 mm, preferably in the range 1 to 3 mm;
h3 is in the range 10 to 100 mm, preferably in the range 20 to 60 mm.

Figure 1:
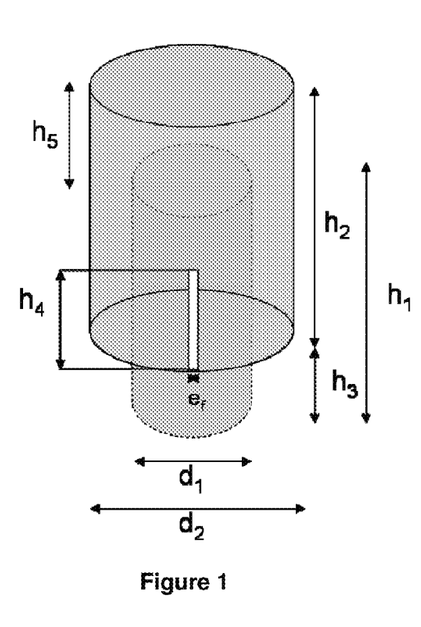
FIG. 1 represents a diagrammatic view of a distributor plate of the invention, showing the outer cylinder 2 and the inner cylinder 1 which constitute the distribution element and in which the outer cylinder 2 is raised by a height h3 with respect to the base plane of the distributor plate.
Figure 2:
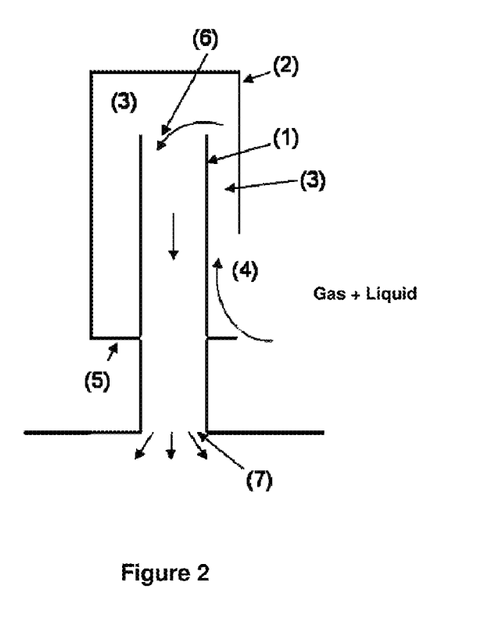
FIG. 2 represents a diagrammatic view of a distributor plate of the invention, showing the outer cylinder 2 and the inner cylinder 1 which constitute the distribution element and in which the outer cylinder 2 is raised by a height h3 with respect to the base plane of the distributor plate.
Figure 3:
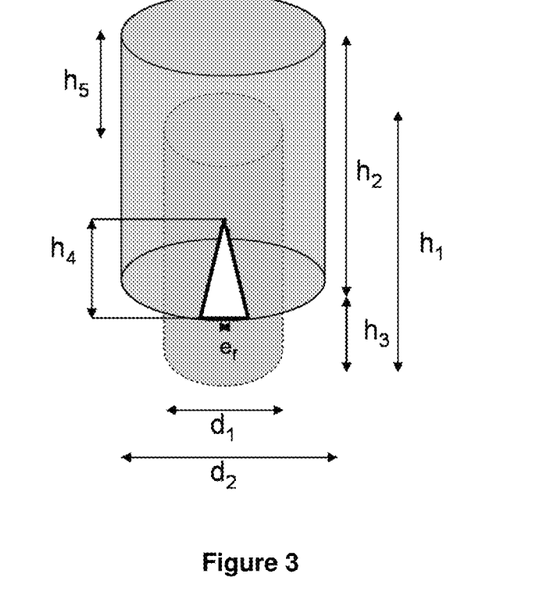
FIG. 3 illustrates the slots for passage of gas and liquid have a triangular shape, the point of the triangle being directed upwardly.
Figure 4:
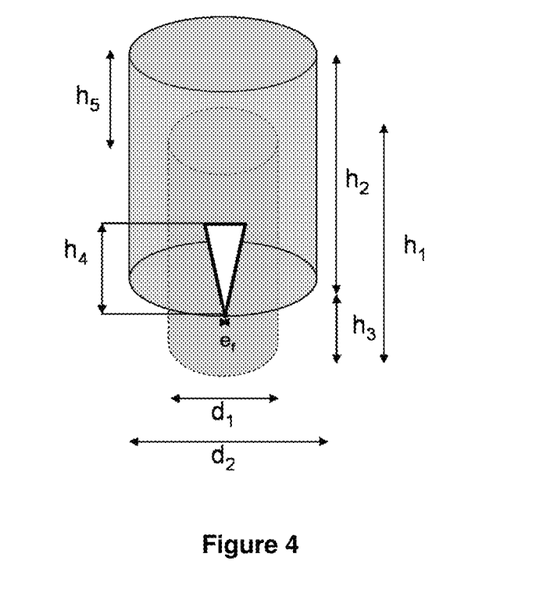
FIG. 4 illustrates the slots for passage of gas and liquid have a triangular shape, the point of the triangle being directed downwardly.

The slots for admitting gas and liquid may have a fairly wide variety of shapes, the simplest and preferred shape being rectangular (h4, ef), or a triangular shape, still characterized by the dimensions h4 and ef, the point of the triangle being directed upwards or downwards.

Figure 5:
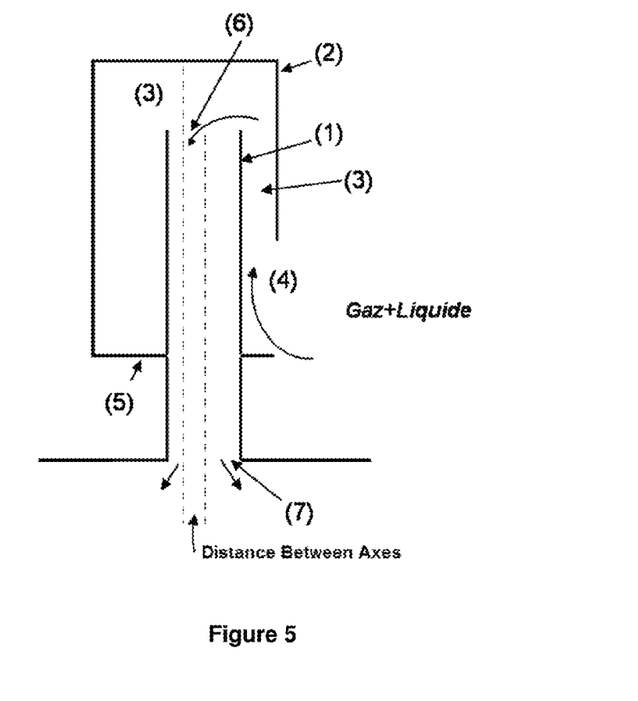
FIG. 5 represents the two cylinders, inner and outer, which are not exactly coaxial but are off-centre by a distance between their two axes (d2−d1)/4.

The distributor plate of the present invention may in some cases have a certain offset between the axes of the two cylinders, inner and outer, which make it up. The expression "substantially" or "approximately" coaxial must be construed in its broadest sense, as the distance between their two axes may be in the range 0 to (d2−d1)/4.

Figure 6:
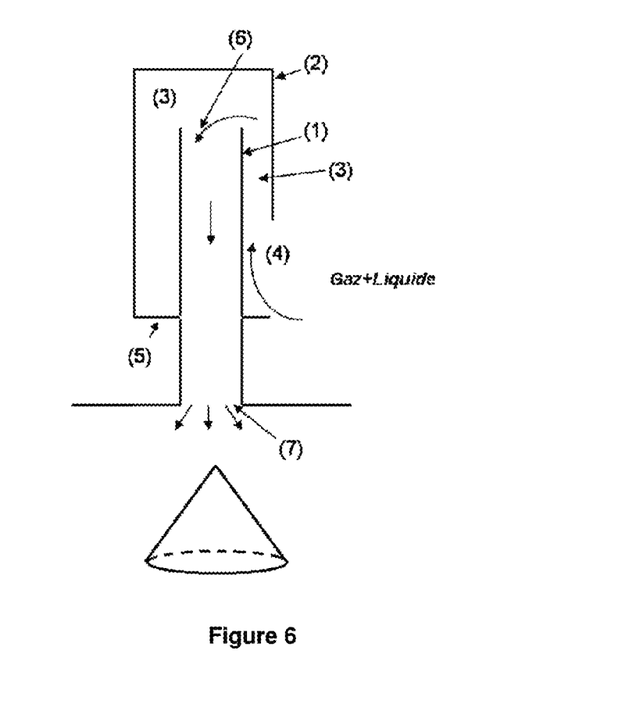
FIG. 6 represents the distributor plate which is completed by a set of conical deflectors forming an integral part of said plate, each deflector being placed beneath a distribution element, the enlarged portion of the cone being directed downwardly.

The distributor plate of the present invention may be completed by a set of conical deflectors, each deflector being placed below a distribution element, the wide portion of the cone being directed downwardly.

In general, any type of deflector which is known to the skilled person may be used in the context of the present invention.

Figure 7:
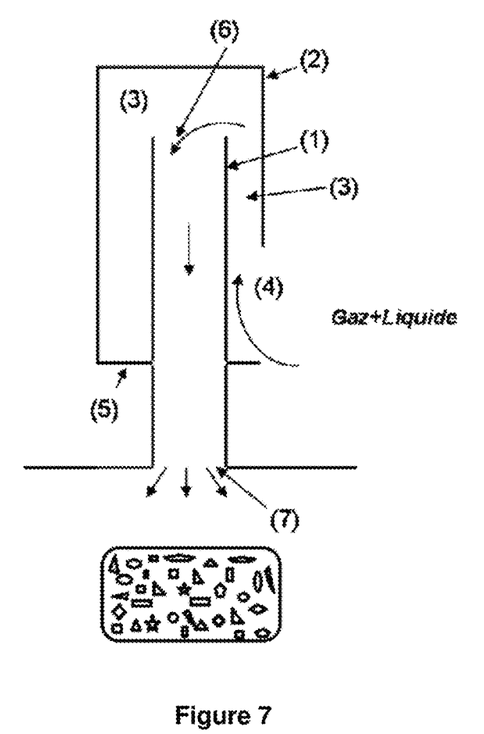
FIG. 7 represents the distributor plate which is completed by a set of screens forming an integral part of said plate and placed downstream of the plate, the various screen elements also being disposed in different planes.

The distributor plate of the present invention may also be completed by a set of screen elements placed downstream of the plate at a distance in the range 20 mm to 300 mm, preferably in the range 50 mm to 150 mm from said plate, the various screen elements also being disposed on different planes. When they are present, these deflectors or screen elements form an integral part of the plate of the invention.

The distributor plate of the present invention is of principal application in reactors carrying out hydrotreatment, hydrogenation or oxidation reactions of oil cuts with a number of carbon atoms of 4 to 30, preferably 8 to 20.

More generally, the distributor plate of the present invention is of application in reactors employing a downflowing co-current of gas and liquid in "trickle bed" mode, i.e. with a surface velocity of the liquid in the range 0.1 to 1.5 cm/s.

DETAILED DESCRIPTION OF THE INVENTION

The invention may be defined as a distributor plate adapted for two-phase gas liquid flows in downflow co-current mode. Such a plate is intended for installation in reactors using this type of two-phase flow, more particularly in "trickle bed" mode, which is defined as a flow in which the continuous phase is the gas phase and the discontinuous phase is the liquid phase, the liquid being present in the form of trickles which are approximately regular, with a surface velocity of the liquid in the range 0.1 to 1.5 cm/s.

The distribution elements are distributed regularly over the distributor plate in a pattern which may be rectangular, square or triangular.

A distribution element is constituted by two approximately coaxial cylinders, the inner cylinder with diameter d1 and the outer cylinder with diameter d2.

These two substantially coaxial cylinders define an annular zone 3 through which the gas and liquid move in upflow mode. The gas and the liquid are in fact admitted into the annular zone 3 via one or more longitudinal slots 4 pierced along the wall of the outer cylinder 2.

The lower portion of the slot in general admits liquid, and the upper portion of the slot in general admits gas. Thus, it is essential that this upper portion of the slot, termed the "dry" slot, is sufficient to admit the gas at the desired flow rate. One of the advantages of the distribution elements of the present invention is that they have low sensitivity to any lack of horizontality due to the height of the dry slot which is always sufficient to allow gas to be admitted into the annular zone 3.

The outer cylinder 2 does not descend to the base of the plate and stops at a height h3 therefrom. The longitudinal slot 4 starts from said height h3 above the plate and extends to a height h3+h4.

The horizontal surface 5 separating the outer cylinder 2 and the inner cylinder 1 is closed.

The number of longitudinal slots 4 is limited to 2 or 3 per distribution element. These various characteristics mean that the function of the distribution elements is substantially improved, in particular in the presence of a lack of horizontality. The fact that the number of slots is reduced and the bottom of the distribution element is closed means that the height of the liquid trap is better controlled, so as to ensure a sufficient dry slot height so that in the event of a lack of horizontality, the distance between the surfaces open to gas between two distribution elements having a certain variation is small.

In contrast to patents US2007/145610 and U.S. Pat. No. 5,942,162, the system does not necessitate confining the two-phase flow in the portion located between the two concentric tubes where the flow is of the gas lift type, as in contact with gas and liquid at the slot, a two-phase emulsion is formed which occupies all of the annular space defined by the substantially coaxial cylinders.

EXAMPLES

The two comparative examples below illustrate the advantages of the distribution system of the present invention compared with two prior art devices.

Example 1

Compares the distribution efficiency of the distribution device of the invention with a standard distributor plate provided with chimneys.

When the plate (of the prior art or of the invention) is subjected to a lack of horizontality of $\Delta H=1$ cm, the sensitivity to the lack of horizontality of the plate is quantified by defining the liquid imbalance index as follows:

$$Iq_L(\%) = \frac{W_{L.chimney1} - Q_{L.chimney2}}{(Q_{L.chimney1} + Q_{L.chimney1})/2} \times 100$$

where:
$Q_{L.chimney1,2}$ is the volume flow rate of liquid leaving the two chimneys with index 1 and 2 of the plate located at a height difference corresponding to the lack of horizontality of $\Delta H=1$ cm.

A low value for the liquid imbalance index indicates a low sensitivity to a lack of horizontality. In contrast, a high value for $Iq_L$ indicates a large imbalance in the distribution.

The standard plate is provided with chimneys pierced with orifices for the passage of liquid distributed over several rows.

The principal characteristics of these standard chimneys were as follows:
- triangular pitch of 200 mm between the chimneys;
- rows of holes at 50/100/150 mm high from the base of the plate;
- chimney height: 250 mm;
- chimney diameter: 50 mm;
- number and size of holes per row: 3 holes of 7 mm.

The configuration of the holes of the chimneys was defined for a range of liquid velocities in the range 0.2 to 1.3 cm/s and for a gas velocity of 15 cm/s.

The distribution elements of the invention had the characteristics given in Table 1 below.

The index 1 refers to the inner cylinder and the index 2 to the outer cylinder.

TABLE 1

| | |
|---|---|
| H4 (mm) | 150 |
| H5 (mm) | 25 |
| H2 (mm) | 320 |
| H3 (mm) | 40 |
| d1 (mm) | 50 |
| d2 (mm) | 110 |
| ef (mm) | 2 |
| No of slots | 1 |

Figure 8:
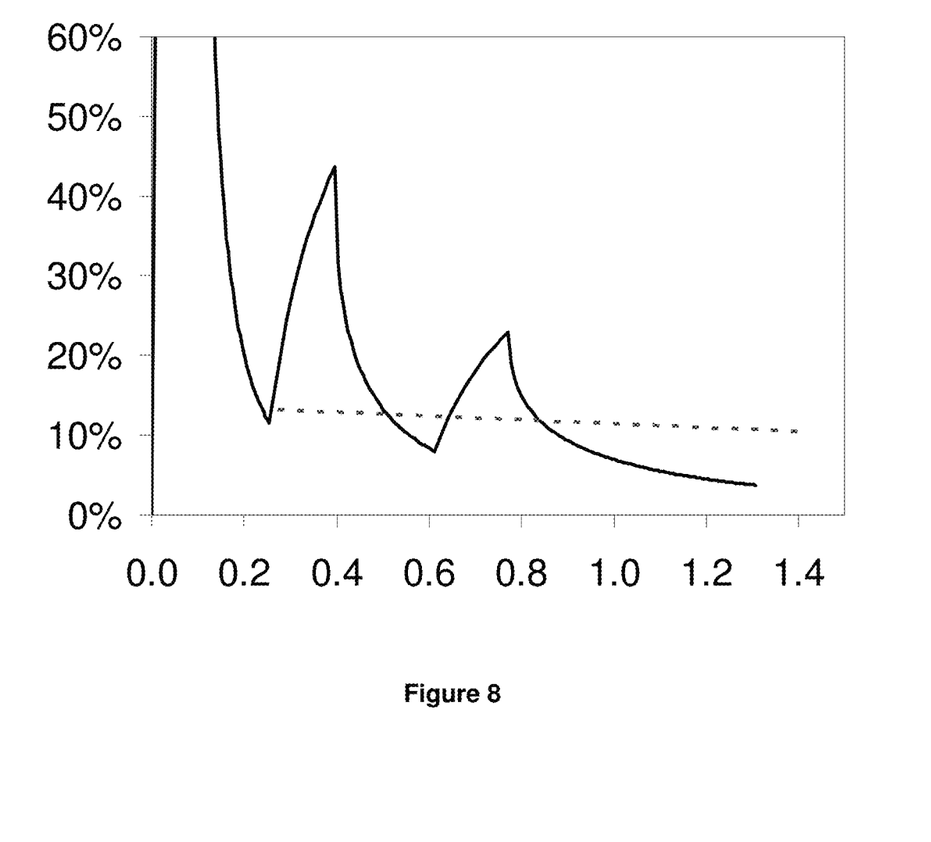
FIG. 8 represents a graph of the variation in the liquid imbalance index (defined below in the description) as a function of the surface velocity of the liquid (Vsl), meaning that the plate of the invention can be compared with a prior art chimney device.

FIG. 8 presents the variation in the liquid imbalance index $Iq_L$ (up the ordinate) as a function of the surface velocity of the liquid $V_{SL}$ (along the abscissa) for the prior art plate (solid line curve) and the plate of the invention (dotted line curve).

For the prior art plate, the liquid imbalance index varied between 5% and 40% over the whole range of $V_{SL}$ under consideration (from 0.1 to 1.3 cm/s) with peaks corresponding to $V_{SL}$ which entrain opening up or obstruction of an orifice.

Thus, there is a highly disadvantageous effect of peaks linked to the discontinuities in the orifices for the passage of gas and liquid.

In contrast, the plate of the invention exhibited stable performance with a liquid imbalance index $Iq_L \approx 13\%$ over the whole functional range of $V_{SL}$.

This example shows that the device of the invention can be used to obtain a significant gain in flexibility and efficiency of distribution in the presence of a lack of horizontality of the plate.

Example 2

Compares the distribution efficiency of the plate of the invention with that of a plate provided with bell-cap chimneys in accordance with the prior art for a lack of horizontality of $\Delta H=1$ cm.

The distribution efficiency was again quantified by the liquid imbalance index $Iq_L$; the surface velocity of the liquid varied from 0.1 to 1.3 cm/s.

The characteristics of the bell-cap chimney plate are given in Table 2 below.

TABLE 2

| Height of bell-cap (mm) | 150 |
| --- | --- |
| Height of bell-cap with respect to base plane of plate (mm) | 40 |
| Height of slot for admission of gas-liquid mixture (mm) | 65 |
| Diameter of inner cylinder (mm) | 50 |
| Diameter of bell-cap (mm) | 100 |
| Width of gas-liquid admission slot (mm) | 22 |
| Number of slots | 3 |

The characteristics of the plate provided with distribution elements in accordance with the invention are given in Table 3 below.

The index 1 again refers to the inner cylinder; the index 2 refers to the outer cylinder.

TABLE 3

| H4 (mm) | 150 |
| --- | --- |
| H5 (mm) | 25 |
| H2 (mm) | 320 |
| H3 (mm) | 40 |
| d1 (mm) | 50 |
| d2 (mm) | 110 |
| ef (mm) | 2 |
| No of slots | 1 |

Figure 9:
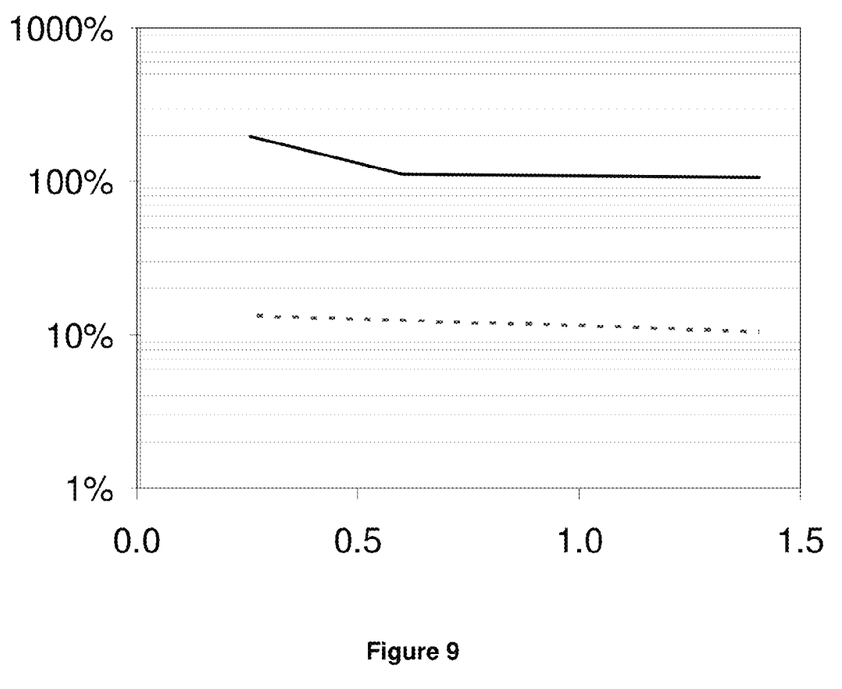
FIG. 9 represents a graph of the variation in the liquid imbalance index (defined below in the description) as a function of the surface velocity of the liquid (Vsl), meaning that the plate of the invention can be compared with a prior art device generally known as a "bell-cap chimney" device.

The variation in the liquid imbalance index $Iq_L$ as a function of the surface velocity of the liquid $V_{SL}$ for the two plates is shown in FIG. 9.

The results show a large sensitivity to a lack of horizontality for the "bell-cap chimney" chimney plates (solid line curve).

In fact, the degree of mal-distribution was more than 100% over the whole functional range of $V_{SL}$.

In contrast, the plate of the invention was less sensitive to an imposed lack of horizontality, the liquid imbalance index over the range of $V_{SL}$ being practically constant around a value of 13% (dotted line curve).

These two examples clearly show the advantage of the plate of the present invention, the latter allowing the effect of a lack of horizontality during installation of the distributor plate to be greatly attenuated, over a range of surface velocity of the liquid of 0.1 to 1.3 cm/s, i.e. corresponding to the "trickle bed" mode for which the plate of the invention is particularly well suited.

The invention claimed is:

1. A distributor plate for a gas-liquid flow in downflow co-current mode positioned at various levels of a reactor which may comprise a plurality of catalytic beds, in order to ensure homogeneous distribution of the resulting gas-liquid mixture over a catalytic bed located downstream of said plate,
said plate being provided with distribution elements distributed regularly over the surface of the plate in a square or triangular pattern, a distribution element containing two substantially coaxial cylinders termed the inner cylinder (1) with a diameter (d1) and height (h1), and the outer cylinder (2) with a diameter (d2) and height (h2), raised by a height (h3) with respect to the plane of the plate, a lower horizontal surface (5) separating the two cylinders being closed and located at a height (h3) above the base of the distributor plate which is in the range of 10 to 100 mm, and the lateral wall of the outer cylinder (2) being provided with at least one substantially vertical slot (4) for admitting gas and liquid into an annular zone (3), the gas-liquid mixture being capable of entraining in the annular zone (3) as an upflowing stream, then passing into the inner cylinder (1) via an upper opening (6) thereof and dropping inside the inner cylinder (1), then evacuated via an opening (7) located at the lower end of the inner cylinder (1).

2. The distributor plate for a gas-liquid flow in downflow co-current mode according to claim 1, in which the number of vertical slots (4) with height (h4) is 1 to 3.

3. The distributor plate for a gas-liquid flow in downflow co-current mode according to claim 1, in which the pitch between the distribution elements is in a square or triangular pattern with a dimension of 100 to 200 mm.

4. The distributor plate for a gas-liquid flow in downflow co-current mode according to claim 1, in which the total height of the distribution elements is in the range of 200 to 400 mm.

5. The distributor plate for a gas-liquid flow in downflow co-current mode according to claim 1, in which
(h2) is in the range of 100 to 500 mm,
(d2) is in the range of 15 to 300 mm,
(h1) is in the range of 100 to 500 mm,
(d1) is in the range of 10 to 100 mm,
(h4) is in the range of 10 to 500 mm,
(ef) is in the range of 1 to 5 mm,
(h3) is in the range of 10 to 100 mm,
wherein
(h2) is the height of outer cylinder,
(d2) is the diameter of outer cylinder,
(h1) is the height of inner cylinder,
(d1) is the diameter of inner cylinder,
(h4) is the height of the admission slot for the gas-liquid mixture,
(ef) is the width of the admission slot for the gas-liquid mixture, and
(h3) is the height of the outer cylinder with respect to the base plane of the plate.

6. The distributor plate for a gas-liquid flow in downflow co-current mode according to claim 1, in which the slots for passage of gas and liquid have a triangular shape, the point of the triangle being directed upwardly or downwardly.

7. The distributor plate for a gas-liquid flow in downflow co-current mode according to claim 1, in which the two cylinders, inner and outer, are not exactly coaxial but are off-centre by a distance between their two axes in the range of greater than 0 to (d2−d1)/4.

8. The distributor plate for a gas-liquid flow in downflow co-current mode according to claim 1, in which the distributor plate is completed by a set of conical deflectors forming an integral part of said plate, each deflector being placed beneath a distribution element, the enlarged portion of the cone being directed downwardly.

9. The distributor plate for a gas-liquid flow in downflow co-current mode according to claim 1, in which the distributor plate is completed by a set of screens forming an integral part of said plate and placed downstream of the plate by a distance in the range of 20 to 300 mm from said plate, the various screen elements also being disposed in different planes.

10. A process for the hydrotreatment, hydrogenation or oxidation of oil cuts containing 4 to 20 carbon atoms, comprising passing a gas or liquid in said process by a distributor plate according to claim 1.

11. A process comprising a co-current downflow of gas and liquid in a trickle bed mode with a surface velocity of liquid in the range of 0.1 to 1.5 cm/s, comprising passing said gas and liquid by a distributor plate according to claim 1.

12. The distributor plate for a gas-liquid flow in downflow co-current mode according to claim 1, wherein (h3) is in the range of 20 to 60 mm.

13. The distributor plate for a gas-liquid flow in downflow co-current mode according to claim 1, in which the number of vertical slots (4) with height (h4) is 1 to 2.

14. The distributor plate for a gas-liquid flow in downflow co-current mode according to claim 5, in which
   (h2) is in the range of 200 to 400 mm,
   (d2) is in the range of 50 to 200 mm,
   (h1) is in the range of 200 to 400 mm,
   (d1) is in the range of 25 to 75 mm,
   (h4) is in the range of 100 to 300 mm,
   (ef) is in the range of 1 to 3 mm, and
   (h3) is in the range of 20 to 60 mm.

15. The distributor plate for a gas-liquid flow in downflow co-current mode according to claim 1, in which the two cylinders, inner and outer, are coaxial.

16. The distributor plate for a gas-liquid flow in downflow co-current mode according to claim 1, in which the distributor plate is completed by a set of screens forming an integral part of said plate and placed downstream of the plate by a distance in the range of 50 to 150 mm from said plate, the various screen elements also being disposed in different planes.

17. A process for the hydrotreatment, hydrogenation or oxidation of oil cuts containing 8 to 20 carbon atoms, comprising passing a gas or liquid in said process by a distributor plate according to claim 1.

18. The distributor plate for a gas-liquid flow in downflow co-current mode according to claim 5, in which one or more of the following apply
   (h2) is in the range of 200 to 400 mm,
   (d2) is in the range of 50 to 200 mm,
   (h1) is in the range of 200 to 400 mm,
   (d1) is in the range of 25 to 75 mm,
   (h4) is in the range of 100 to 300 mm,
   (ef) is in the range of 1 to 3 mm, and
   (h3) is in the range of 20 to 60 mm.

19. A distributor plate for a gas-liquid flow in downflow co-current mode positioned at various levels of a reactor which may comprise a plurality of catalytic beds, in order to ensure homogeneous distribution of the resulting gas-liquid mixture over a catalytic bed located downstream of said plate,
   said plate being provided with identical distribution elements distributed regularly over the surface of the plate in a square or triangular pattern, a distribution element containing two substantially coaxial cylinders termed the inner cylinder (1) with a diameter (d1) and height (h1), and the outer cylinder (2) with a diameter (d2) and height (h2), raised by a height (h3) with respect to the plane of the plate, a lower horizontal surface (5) separating the two cylinders being closed and located at a height (h3) above the base of the distributor plate which is in the range of 10 to 100 mm, and the lateral wall of the outer cylinder (2) being provided with one or more identical substantially vertical slots (4) for admitting gas and liquid into an annular zone (3), the gas-liquid mixture being capable of entraining in the annular zone (3) as an upflowing stream, then passing into the inner cylinder (1) via an upper opening (6) thereof and dropping inside the inner cylinder (1), then evacuated via an opening (7) located at the lower end of the inner cylinder (1).

\* \* \* \* \*